United States Patent [19]

Dehuysser

[11] 4,401,893

[45] Aug. 30, 1983

[54] METHOD AND APPARATUS FOR OPTICALLY INSPECTING A MOVING WEB OF GLASS

[75] Inventor: Andre Dehuysser, Brussels, Belgium

[73] Assignee: Intec Corporation, Trumbull, Conn.

[21] Appl. No.: 288,010

[22] Filed: Jul. 29, 1981

[51] Int. Cl.³ .............................................. G01N 21/32
[52] U.S. Cl. .................................... 250/572; 356/239
[58] Field of Search ........... 250/571, 572, 563, 223 B; 364/473; 356/431, 239, 240; 209/526

[56] References Cited

U.S. PATENT DOCUMENTS 3,652,863  3/1972  Gaskell et al. ....................... 356/239
3,859,537  1/1975  Wolf ..................................... 250/563

Primary Examiner—David C. Nelms
Assistant Examiner—J. Jon Brophy

[57] ABSTRACT

An automatic optical inspection of a moving web of glass for defects is provided by transversely scanning a moving web of glass with a light source which is internally reflected within the glass and travels towards the edge of the glass when the scanning light source strikes defects within the web. The light leaving the edges of the glass as a result of internal reflection is captured on opposite edges of the glass web. The captured light is detected and converted to electrical signals which are utilized to determine whether defects are present in the glass web in accordance with the characteristics of the electrical signals so generated. An apparatus is provided for the inspection method which includes edge detectors having a mouthlike construction fitting over the edges of the glass web and collecting internally reflected radiation from the edges of the web and applying it to photomultiplier tubes which are cooled. The mouthlike structure is made completely light tight by having brushes mounted thereon which do not scratch or alter the glass product surface. The edge detectors are enslaved mechanically so as to follow the movements of the glass web so that the system will not disturb the manufacturing process. Since internal reflection is the detection mechanism, and dirt on the surface does not scatter light internally, this method differentiates between dirt, the detection of which is not desired, and defects in optical contact with and under the surface of the glass which are desired to be detected.

8 Claims, 4 Drawing Figures

SPECTRAL TRANSMITTANCE OF FLOAT GLASS

• CLEAR
× GREY
○ BRONZE
△ GREEN

METHOD AND APPARATUS FOR OPTICALLY INSPECTING A MOVING WEB OF GLASS

BACKGROUND OF THE INVENTION

This invention relates to a method and apparatus for automatically optically inspecting a glass web, and more particularly to such a method and apparatus which utilizes internal reflection moving from defects in the web toward the edges and edge detecting the totally internally reflected light at the edges thereof.

The imposition of stringent quality restrictions on the manufacture of float glass presents a serious inspection problem. The type of flaws, the number and where they are located within the glass web is a difficult task for human inspection. With insufficient product knowledge, it is difficult to determine what portion of the glass must be scrapped, which can be salvaged and how to prevent wasted time and materials in the manufacturing process.

Amont the many problems are the detection of bubbles in the glass which are caused by gases captured by the molten elements during the heating process. Such bubbles do not have time to emerge before the glass leaves the heating process. The bubbles vary in size from microns to several centimeters and their size and number vary with the thickness of the glass. Bubbles may be classified as filled bubbles or salt cakes which look like stones and occur infrequently; body bubbles which are small in diameter, relative to the thickness of the glass, which do not distort the glass and appear as small, spherical or eliptical lines and block transmitted light in the glass; or surface bubbles which tend to appear just below the surface of the glass, mostly on the lower surface in float glass and cause distortion in the glass and as an extreme case provide an open bubble when the bubble breaks on the surface.

Bubbles vary greatly in shape from spherical to ellipsoidal with the larger bubbles tending to be more elongated as well as those which are generated in higher speed glass lines. The most important factors in determining the bubble shape are the operating characteristics of a particular float line for manufacturing the glass.

Traditionally bubble detection is done visibly by inspectors with the glass being lit or illuminated from the top such that the defect casts a characteristic shadow on a white board under the glass web. Through training and experience glass inspectors can learn to identify certain kinds of flaws. When a flaw is identified, the location must be marked with a colored crayon attached to the end of a long pointer. However, a great deal of subjective judgment is involved, the accuracy depends on the experience of the inspector, the speed of the line and of course the foibles of human perceptions and response.

SUMMARY OF THE INVENTION

Accordingly, it is an object of this invention to provide a new and improved method and apparatus for automatically optically inspecting a moving web of glass for defects therein.

A further object of this invention is to provide a new and improved apparatus and method of optically inspecting a moving web of glass which eliminates the subjective nature of visual inspection.

A further object of this invention is to provide a new and improved method and apparatus for optically inspecting a moving web of glass for defects which is fast, efficient, more accurate and less time consuming than previously used visual methods.

In carrying out this invention, in one illustrative embodiment thereof, a method of automatically optically inspecting a moving web of glass is provided in which the moving web of glass is scanned orthogonally with respect to the direction of movement with a light source. As the light source strikes a defect within the web, it is internally reflected in the glass and travels towards the edges where it is captured on the opposite ends of the glass web. The captured light emanating from the edges of the web caused by internal reflection due to defects in the glass is detected for converting the light to electrical signals and the defects are determined in accordance with the characteristics of the electrical signals so generated.

Apparatus is provided for carrying out the aforesaid method including edge detection means which surround opposite sides of the web and prevent ambient light from entering the edge detectors. The edge detectors are also cooled and follow the vertical and horizontal motions of the web so as not to disturb the manufacture of the web.

BRIEF SUMMARY OF THE DRAWINGS

The invention, together with further objects, advantages, features and aspects thereof will be more clearly understood from the following description taken in conjunction with the accompanying drawings.

DESCRIPTION OF THE PREFERRED EMBODIMENTS

Figure 1:
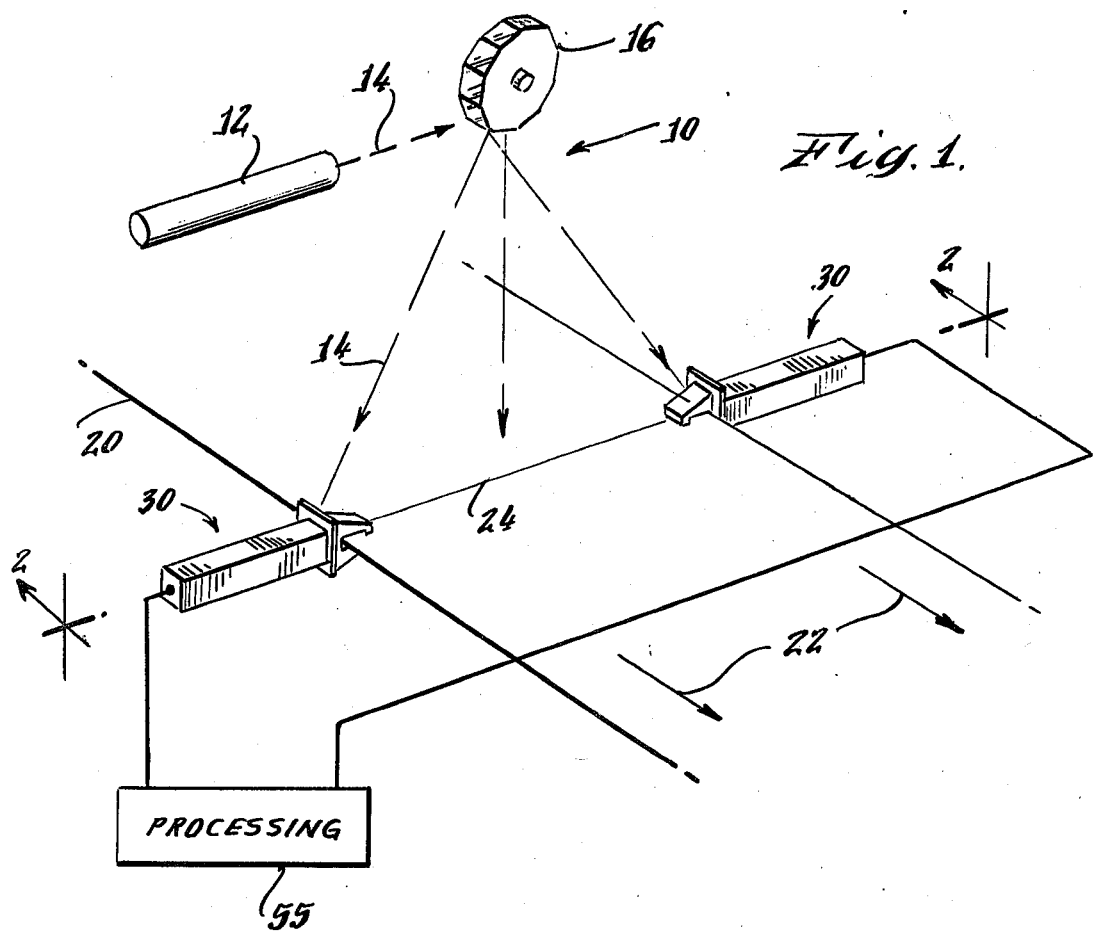
FIG. 1 is a perspective view showing an illustrative embodiment of apparatus for automatically optically inspecting a moving web of glass in accordance with the present invention.

Referring now to FIG. 1, a light inspection system, referred to generally with the reference numeral 10, has a suitable light source such as a laser beam, xenon lamp, etc. generating a beam 14 which is scanned by a scanner 16 over a moving web of glass 20 which is being examined thereby. The scanner 16 may be a conventional, multiple faceted, mirrored surface polygon of a suitable number of facets. However, it will be appreciated that the scanner 16 may comprise any means which functions to rapidly scan a light source across the surface of the glass web 20, such as an oscillating mirror, rotating mirror or prism, or any other suitable deflection apparatus.

The scanner 16 performs the function of scanning the light source repeatedly across the moving web of glass 20 which is moving in the direction shown by the arrows 22 which may be referred to as the machine direction or axis of web movement. As illustrated in FIG. 1, the scanning light beam 14 traces a line 24 across the moving web of glass 20. Scanning in the orthogonal direction is automatically formed by the movement of the glass web 20.

Under ordinary operating conditions, the scanning of the glass web 20 by the light beam 14 causes the beam 14 to be partially reflected from the top surface of the glass web 20 with a portion of the beam being refracted by the glass web 20 as well as being absorbed thereby. On the other hand, if a bubble impairment or defect exists in the glass as it is scanned by the beam 14, the light will impinge on the abnormality and be deflected thereby producing an angle of reflection which satisfies the critical angle and causes total internal reflection within the glass which travels towards the edges of the glass web 20. Of course, some of the totally internal reflected light is absorbed as it moves towards the edges.

Figure 2:
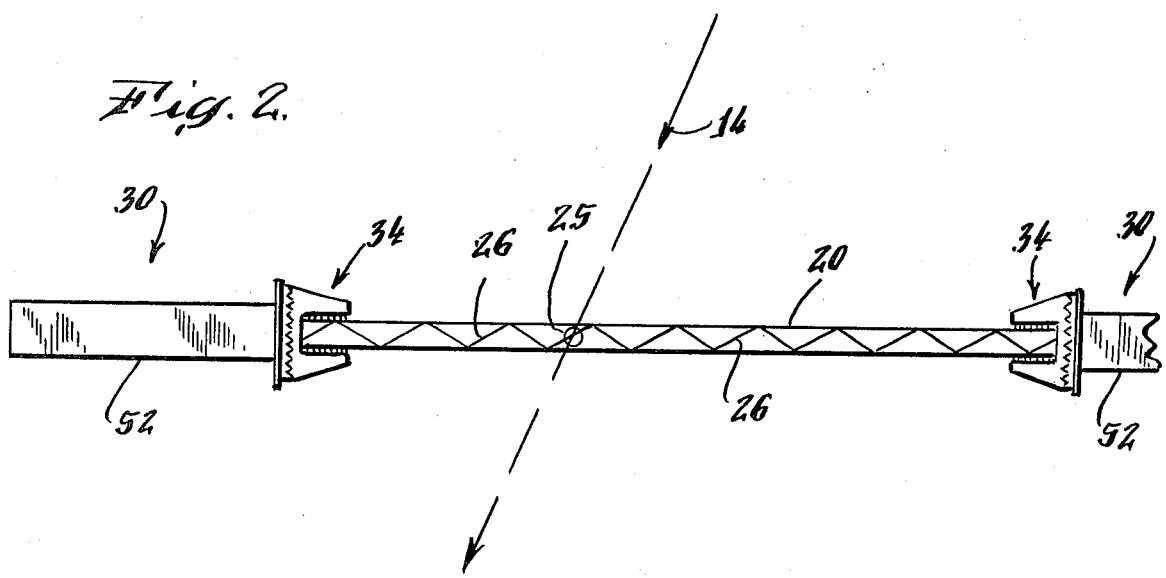
FIG. 2 is a cross-sectional view taken along line 2—2 of FIG. 1.

FIG. 2 illustrates this phenomena with the scanning light beam 14 striking a bubble 25 totally internally reflecting the resulting beam 26 which by total internal reflection is trapped in the glass web. The beam 26 moves to the edges where it may be captured and detected. The intensity of the total reflected beam 26 appearing at the edge of the glass plate 20 is a function of the illumination wavelength, the distance between the edge and the bubble, and the initial intensity of the scanner beam 14.

In order to capture and detect the internally reflected beam 26, edge detectors, referred to generally with the reference numeral 30, are provided flanking both edges of the moving glass web 20. Of course, the function of the edge detector is to capture the reflected light 26 that emerges from the edges of the glass web 20 on a float line without being disturbed by ambient or stray light due to dust or foreign matter on the glass surface, and further to convert such light into an electrical signal which may be utilized to identify and characterize the flaw which is present. A suitable light detector such as a photomultiplier tube 32 is utilized for converting the internally reflected light appearing at the edges of the web 20 into an electrical signal.

Figure 3:
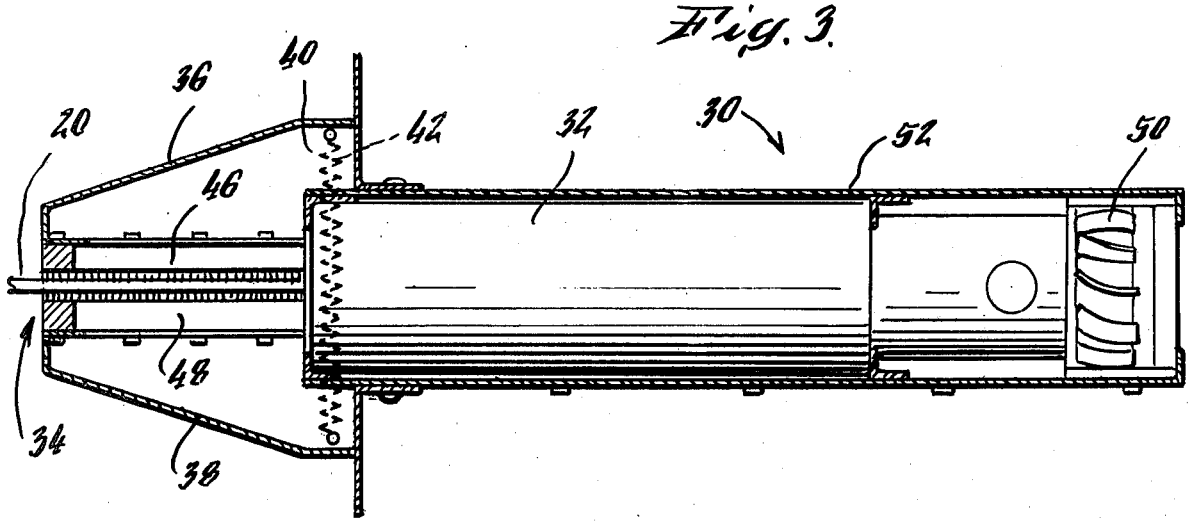
FIG. 3 is a side elevational view of an edge detector assembly which may be utilized in the present invention.

Edge detector 30 includes a number of features due to the conditions which it must operate under including a warm glass web which may be dusty, wet and moving in all directions as well as having varying amounts of ambient light which must be excluded and not measured. The construction of the edge detector 30, as best seen in FIG. 3 includes a mouth 34 that fits over the glass edge such that only the edges of the glass are seen by the detector or photomultiplier tube 32. The mouth 45 has upper and lower jaws 36 and 38 with the jaws being movable in order to follow the glass web. The jaws are held by springs 40 mounted on a vertical rail 42. The detectors 30 may be moved manually in the horizontal direction because the horizontal movements are very slow. However, the horizontal movement may also be done mechanically. A preferable way of moving the edge detectors 30 along the web would be by providing glass edge sensors which operate pneumatic cylinders to follow the horizontal and vertical movements of the web.

Since it is desired to exclude ambient light from the face of the photomultiplier tube, the mouth 34 is equipped with upper and lower brushes 46 and 48, respectively, which completely seal the mouth in a light tight condition without scratching or altering the glass product. The brushes 46 and 48 may be carbon filter or other resistant material mounted in a light labyrinth construction.

Since the photomultiplier tube 32 has a noise characteristic proportional to temperature, and since the float glass and the ambient air are warm at the inspection site, typically between 40° and 60°, cooling of the tube becomes necessary. Accordingly, a fan 50 is provided for blowing air in the detector housing 52. By filtering the air inside, the detector housing can be kept dust free by creating an overpressure in the air stream which also prevents water which is normally present on the web edges from condensing on the photomultiplier tube window.

In operation the source 10 which generates the beam 14 is scanned by the scanner 16 orthogonally across the glass web being inspected. The edge detectors 30 fit over the glass edges and capture the light which is internally reflected toward the edges of the glass web 20 due to defects occurring in the glass web which have been struck by the scanning light beam 14 and have been caused to be totally internally reflected to the edges of the glass web. The brushes 46 and 48 on the jaws 36 and 38 of the mouth 34 mechanically follow the movements or the motions of the web and follow the web without admitting ambient light thereto and without scratching or altering the product. As will be seen in FIG. 1 the electrical signals which are generated by the detector 32 are applied to a processing circuit 55 from which flaws or defects may be characterized depending on their location and size and type. Generally speaking, the signals generated must exceed a predetermined amplitude which takes care of system anomalies and noise and indicates that a flaw exists and that a flaw signal rather than noise has triggered the output of the processing circuit 55. The signal processing techniques per se are considered conventional and accordingly are not discussed in detail. Reference may be made to U.S. Pat. Nos. 3,781,531; 3,900,265; 3,920,970; 3,898,469 and 3,980,891 which are assigned to the assignee of the present invention for information with respect to signal processing. The exact nature and type of processing used will depend on the characteristics of the material being inspected and the particular application to which the processing is employed.

Figure 4:
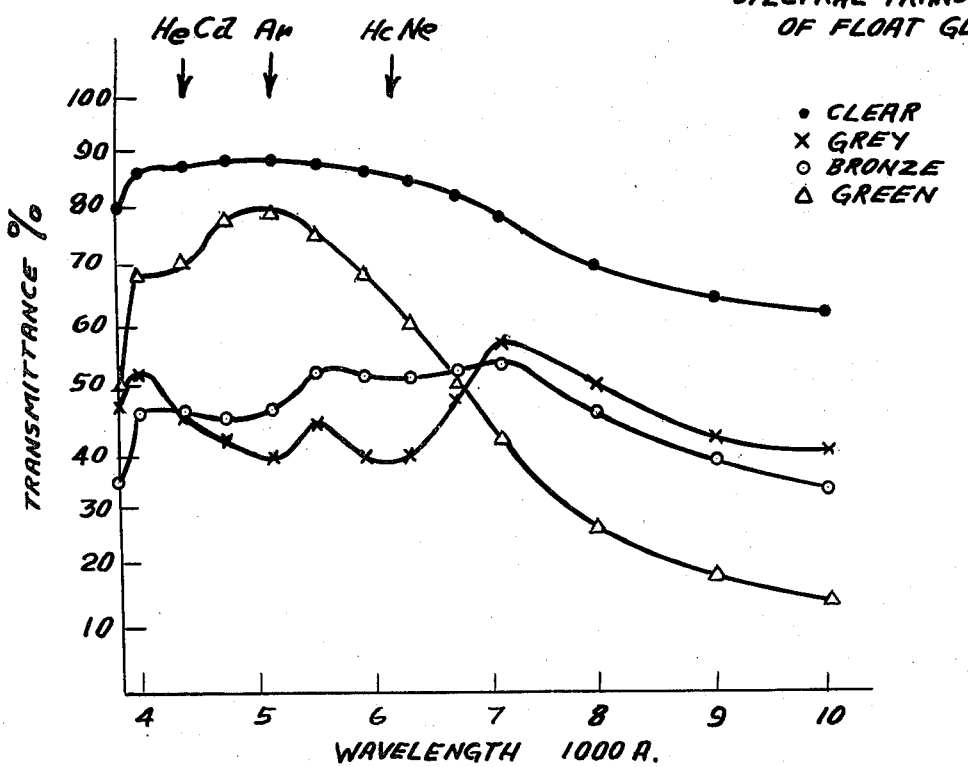
FIG. 4 is a graph illustrating the spectral transmittance of several types of float glass.

FIG. 4 is a graph illustrating the spectral transmittance of float glass verses wavelength indicating the wavelength of a helium cadmium laser, an argon laser or a helium laser. Due to its properties, clear glass has a slightly green appearance which is readily visible in thick glass plates. Accordingly, clear glass transmits visible light almost independently of color with the best transmission for green being about 500 nanometers. When light hits a flat glass surface about 8 percent of the light is reflected and about 2 percent is absorbed per centimeter. Accordingly, FIG. 4 provides a relation between the absorptions for different wavelengths in clear and various colored glasses. The type of source which is utilized will therefore depend to some extent on the type of float glass which is being examined.

By utilizing total internal reflection and monitoring the light emanating from the edges caused by the flaws provides a tool which may be utilized in combination with others to form reliable detection on a very high percentage of glass defects. Thus, the edge detector system may be used by itself or it may be used in conjunction with a receiver which detects the reflected light off of the top surface of the glass and/or the light which is transmitted through the glass by placing the receiver on the underside and processing the radiation therefrom. By utilizing these combined approaches, a more fully automatic and reliable automatic optical inspection system provides a complete diagnostic tool for the examination of float glass. Furthermore, this method and approach to the inspection of glass provides a way of distinguishing between surface dirt and actual defects in surface and in the glass.

Since other changes and modifications varied to fit particular operating requirements and environments will be apparent to those skilled in the art, the invention is not considered limited to the examples chosen for purpose of illustration, and covers all changes and modifications which do not constitute a departure from the true spirit and scope of this invention.

What is claimed is:

1. The method of automatically optically inspecting a moving web of glass for defects comprising the steps of:
   transversely scanning the moving web of glass with a light source,
   internally reflecting the scanning light source within the glass which travels toward the edges when it strikes defects within the web,
   capturing the light that leaves the glass on opposite edges of said glass web,
   detecting the captured light for converting the light to electrical signals, and
   determining whether defects are present in said glass web in accordance with the characteristics of said electrical signals.

2. The method set forth in claim 1 including the step of blocking ambient light from entering the edges of the glass web so that such ambient light is not captured with the internal reflected light.

3. The method set forth in claims 1 or 2 including the step of tracking the horizontal and vertical motions of the glass web as the captured light is detected.

4. An automatic optical inspection system for inspecting a moving web of glass comprising:
   a light source,
   scanning means for scanning said light source orthogonally across said moving glass web,
   said light source being internally reflected within said glass web toward the edges thereof when said light source strikes a defect therein,
   collecting means positioned on opposite edges of said glass web for capturing the light emerging from the edges of said glass web,
   detector means having said collecting means coupled thereto for applying the radiation gathered by said collecting means to said detector means,
   said detector means generating electrical signals in accordance with the intensity of the light applied thereto which may be used for determining defects in the glass web.

5. The optical inspection system set forth in claim 4 in which said collecting means includes a mouth having movable jaws thereon which are adapted to be mounted on and conform generally with the configuration of the edges of said glass web.

6. The optical inspection system set forth in claim 4 or 5 including tracking means coupled to said collecting means for directing said collecting means to follow the movements of said web.

7. The optical inspection system set forth in claim 5 in which said jaws have brushes mounted thereon for eliminating ambient air from the edges of the glass web when the jaws of said mouth are mounted thereon.

8. The optical inspection system set forth in claim 4 in which at least one collecting means and detector means are mounted in a common housing and means in said housing for cooling said detector means.

* * * * *